US011723549B2

(12) United States Patent
Kremeier et al.

(10) Patent No.: US 11,723,549 B2
(45) Date of Patent: Aug. 15, 2023

(54) SYSTEM FOR CAPTURING RESPIRATORY EFFORT OF A PATIENT

(71) Applicant: Loewenstein Medical Technology S.A., Luxembourg (LU)

(72) Inventors: Peter Kremeier, Karlsruhe (DE); Sven Pulletz, Osnabrueck (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 686 days.

(21) Appl. No.: 16/794,135

(22) Filed: Feb. 18, 2020

(65) Prior Publication Data

US 2020/0260985 A1     Aug. 20, 2020

(30) Foreign Application Priority Data

Feb. 20, 2019    (DE) .......................... 102019104337.9

(51) Int. Cl.
*A61B 5/0536*     (2021.01)
*A61B 5/08*        (2006.01)
(Continued)

(52) U.S. Cl.
CPC .......... *A61B 5/0536* (2013.01); *A61B 5/0036* (2018.08); *A61B 5/085* (2013.01);
(Continued)

(58) Field of Classification Search
CPC ..... A61B 5/0036; A61B 5/053; A61B 5/0535; A61B 5/0536; A61B 5/0809; A61B 5/0833; A61B 5/0836; A61B 5/085; A61B 5/1135; A61B 5/7239; A61B 5/7264; A61B 5/7285; A61B 5/7292; A61M 16/00; A61M 16/0003; A61M 16/0021; A61M 16/0027; A61M 16/0033; A61M 16/022; A61M 16/024; A61M 16/0247; A61M 16/205; A61M 2205/3331; A61M 2230/65; A61M 2016/0024; A61M 2205/3317; A61M 2205/502; A61M 2205/52; A61M 2210/1039
See application file for complete search history.

(56) References Cited

U.S. PATENT DOCUMENTS 5,544,662 A    8/1996   Saulnier et al.
10,154,796 B2   12/2018   Choi et al.
(Continued)

FOREIGN PATENT DOCUMENTS

CN       106540364 A    3/2017
DE     102012224522 A1    7/2013
(Continued)

*Primary Examiner* — Brian T Gedeon
(74) *Attorney, Agent, or Firm* — Abel Schillinger, LLP

(57) ABSTRACT

An apparatus for capturing the electrical behavior of the human body during respiration and/or ventilation, the apparatus comprising ventilation elements, elements for capturing the impedance of the patient and at least one control unit. The impedance is captured using at least two electrically conductive electrodes, which capture the electrical behavior of the human body. The elements for capturing the impedance are configured to capture the change in the impedance of the human body over time during respiration and/or ventilation.

20 Claims, 5 Drawing Sheets

(51) Int. Cl.
    *A61B 5/085*     (2006.01)
    *A61M 16/00*     (2006.01)
    *A61M 16/20*     (2006.01)
    *A61B 5/00*     (2006.01)
    *A61B 5/083*     (2006.01)

(52) U.S. Cl.
    CPC .......... *A61B 5/0809* (2013.01); *A61B 5/0816* (2013.01); *A61B 5/0833* (2013.01); *A61B 5/0836* (2013.01); *A61B 5/7239* (2013.01); *A61B 5/7264* (2013.01); *A61M 16/00* (2013.01); *A61M 16/022* (2017.08); *A61M 16/024* (2017.08); *A61B 2562/0247* (2013.01); *A61M 16/205* (2014.02); *A61M 2016/0021* (2013.01); *A61M 2016/0027* (2013.01); *A61M 2016/0033* (2013.01); *A61M 2205/3331* (2013.01); *A61M 2230/65* (2013.01)

(56) References Cited

U.S. PATENT DOCUMENTS

| | | |
|---|---|---|
| 2004/0130338 A1 | 7/2004 | Wang et al. |
| 2005/0065447 A1* | 3/2005 | Lee ................ A61B 5/4806 600/529 |
| 2006/0278223 A1 | 12/2006 | Younes |
| 2010/0228143 A1 | 9/2010 | Teschner et al. |
| 2011/0245711 A1 | 10/2011 | Katra et al. |
| 2013/0172718 A1 | 7/2013 | Choi et al. |
| 2015/0272474 A1* | 10/2015 | Genc ................ A61B 5/0809 600/533 |
| 2016/0008561 A1 | 1/2016 | Novotni et al. |

FOREIGN PATENT DOCUMENTS

| | | |
|---|---|---|
| DE | 102013203177 A1 | 8/2014 |
| EP | 2228009 A1 | 9/2010 |
| WO | 02053029 A1 | 7/2002 |

\* cited by examiner

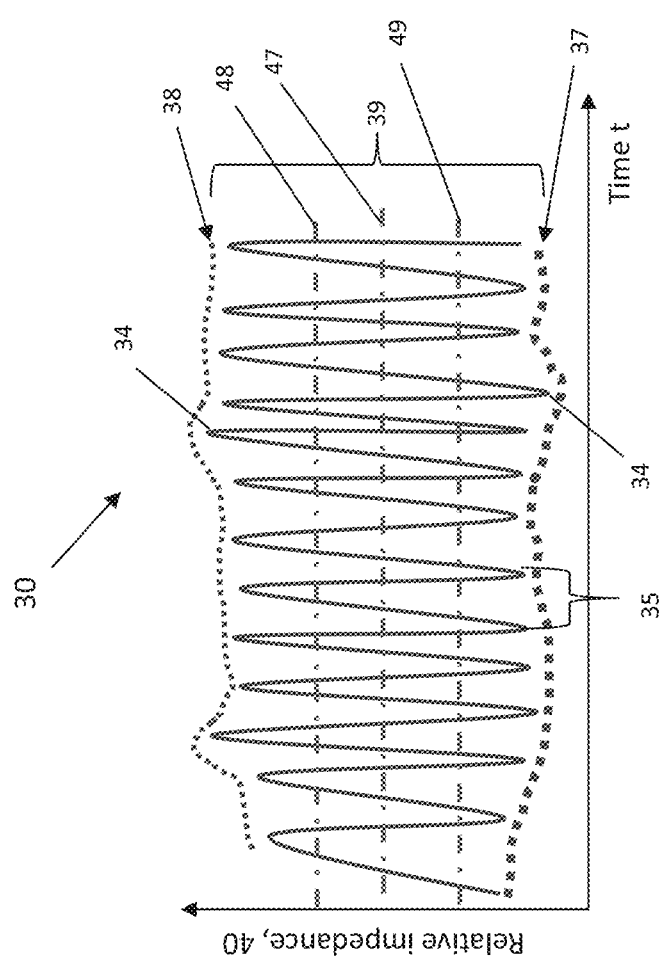

SYSTEM FOR CAPTURING RESPIRATORY EFFORT OF A PATIENT

CROSS-REFERENCE TO RELATED APPLICATIONS

The present application claims priority under 35 U.S.C. § 119 of German Patent Application No. 102019104337.9, filed Feb. 20, 2020, the entire disclosure of which is expressly incorporated by reference herein.

BACKGROUND OF THE INVENTION

1. Field of the Invention

This invention relates to a method for measuring the change in the electrical impedance of a body part, during respiration/ventilation, using electrically conductive electrodes.

Further, the invention relates to an apparatus that is suited and configured to ascertain the change in the electrical impedance of a body part, during respiration/ventilation, using electrically conductive electrodes.

In general, this invention relates to electrical impedance analysis (EI) and, for example, to electrical impedance tomography (EIT). A conventional method for obtaining image data by means of EIT is to feed an electrical current into a pair of conducting electrodes and measure potentials that are produced between another pair of conducting electrodes.

2. Discussion of Background Information

EIT is used in the field of medical imaging as an alternative to computed tomography scanning (CT scanning) or magnetic resonance imaging (MRI). Compared to the alternatives, EIT has the advantages of being noninvasive, not causing irradiation damage and allowing long-term monitoring. By contrast, the image resolution is lower than in the alternative methods. In recent years, EIT technology has been developed with the goal of further improving the image resolution. DE 102012224522 A1, WO 2002053029 A1 and U.S. Pat. No. 5,544,662, the entire disclosures of which are incorporated by reference herein, disclose methods for improving the image resolution of EIT. In particular, EIT technology is used for monitoring and pictorially representing the lung and the gas distribution within the lung of a breathing living being.

These known EIT technologies require complicated electrode arrangements, computer units and calculation algorithms that estimate the distribution of the electrical impedance in the thorax from the voltages measured by means of the electrodes by using algorithms. Moreover, EIT imaging algorithms and much computational power are required to produce individual images from the distribution of the electrical impedance and, subsequently, to produce a multiplicity of images in order to pictorially represent the progress during respiration.

In view of the foregoing, it is desirable to develop a method and an apparatus for quickly and effectively ascertaining the electrical impedance (EI) and for merely capturing and evaluating changes in the impedance. It has unexpectedly been discovered that many information items relevant to ventilation can already be obtained from changes in the impedance over time during respiration/ventilation. It also has been discovered that the information about the changes in the impedance over time during respiration/ventilation is more important than the complicated production of image data.

Disadvantages of the current EIT techniques are overcome thereby. Therefore, the invention encompasses a method and an apparatus for quickly and effectively ascertaining the electrical impedance (EI) over time during respiration/ventilation without having to obtain an image information item therefrom.

SUMMARY OF THE INVENTION

The apparatus for capturing the electrical behavior of a living body during respiration and/or ventilation comprises ventilation elements, elements for capturing the impedance of the living body and at least one control unit. The impedance is captured using at least two electrically conductive electrodes, which capture the electrical behavior of the living body, the elements for capturing the impedance being configured to capture the change in the impedance of the living body over time during respiration and/or ventilation. The ventilation elements (e.g., a ventilator) are configured to stipulate respiratory gas volumes for inspiration and expiration alternately in time. The control unit, at least intermittently, evaluates information items about the impedance and information items about the respiration and/or ventilation.

The apparatus may also be characterized in that the control unit displays and/or records the curve of the impedance over the time curve of the respiration and/or ventilation.

The apparatus may also be characterized in that the control unit determines the slope of the (current) impedance, the slope being able to adopt positive and negative values (polarity of the slope) or being able to equal zero.

The apparatus may also be characterized in that the control unit is also configured to determine whether inspiration or expiration is present from the polarity of the slope.

The control unit may be configured to identify, in the case of a slope with a first polarity, a flattening of the slope of the impedance (which may tend to zero) and to subsequently identify a slope with a second polarity.

The control unit may be configured to interpret the change in the polarity of the slope as the region of an end-expiratory impedance or an end-inspiratory impedance.

The control unit may be configured to interpret the change in the polarity of the slope as the region of a trigger time.

The apparatus may also be characterized in that the control unit is also configured to capture a flattening of the slope of the impedance, the control unit interpreting a flattening of the slope as an approach to a value of maximum or minimum impedance.

The apparatus may also be characterized in that the control unit is configured to ascertain the transition to a point where the slope is substantially zero following the identification of a flattening of the slope of the impedance and to interpret said point as a value of the maximum or the minimum impedance.

The apparatus may also be characterized in that the control unit classifies maximum values of the impedance as inspiratory impedance.

The apparatus may also be characterized in that the control unit classifies minimum values of the impedance as expiratory impedance.

The apparatus may also be characterized in that a threshold is set and/or automatically ascertained for the inspiratory impedance.

The apparatus may also be characterized in that impedances that lie below the threshold are assessed as failed triggers.

The apparatus may also be characterized in that inspiratory impedances that lie below the threshold are assessed as failed triggers.

The apparatus may also be characterized in that impedances that lie above a temporally directly preceding minimum value of the impedance but lie below the threshold are assessed as failed triggers.

The apparatus may also be characterized in that failed triggers are registered and stored and/or transmitted to the ventilator and/or the impedance monitor.

The apparatus may also be characterized in that the failed triggers are directly visualized in the region of a display or stored in recallable fashion by the ventilator and/or the impedance monitor.

The apparatus may also be characterized in that the control unit determines the frequency of the respiration/ventilation from the change of increasing and decreasing impedance over time.

The apparatus may also be characterized in that the control unit uses the end-inspiratory impedance as a trigger criterion for controlling the subsequent expiration by the ventilator.

The apparatus may also be characterized in that the control unit uses the end-expiratory impedance as a trigger criterion for controlling the subsequent inspiration by the ventilator.

The apparatus may also be characterized in that the control unit compares the frequency of the ventilation target with the inherent frequency of the patient, which is determined from the impedance.

The apparatus may also be characterized in that the control unit compares the frequency of the ventilation target with the inherent frequency of the patient, determined from the impedance and/or the flow or the pressure.

The apparatus may also be characterized in that the control unit compares the time of the ventilation target to the time of the impedance signal.

The apparatus may also be characterized in that the impedance information item is used by the control unit to assess the mechanical pressure and volume load under ventilation and accordingly adapts the target of the ventilation.

The apparatus may also be characterized in that a first PEEP pressure is stipulated for at least one instance of respiration and/or ventilation by the control unit and, in the process, a first end-expiratory impedance is ascertained and a second PEEP pressure is stipulated for at least one instance of respiration and/or ventilation and, in the process, a second end-expiratory impedance is ascertained, and at least the first and the second (or any further) end-expiratory impedances are compared to one another and a recommendation for the PEEP pressure that causes the lowest end-expiratory impedance is stored or output for the operator of the ventilator or there is an automatic selection and application of this PEEP pressure.

The apparatus may also be characterized in that the control unit ascertains an impedance variation from at least one maximum value of the impedance and at least one minimum value of the impedance.

The apparatus may also be characterized in that the impedance variation is ascertained and used to adaptively alter at least one ventilation setting, such as, e.g., pressure, PEEP, the pressure control in expiration, frequency, volume and/or else the sensitivity of the sensors, in such a way that the impedance variation increases.

The apparatus may also be characterized in that a first ventilation setting is stipulated for at least one instance of respiration and/or ventilation and, in the process, a first impedance variation is ascertained and, subsequently, a second ventilation setting is stipulated for at least one instance of respiration and/or ventilation and, in the process, the one second impedance variation is ascertained and at least the first and the second (or any further) impedance variations are compared to one another and a recommendation for the ventilation setting that causes the highest impedance variation is stored or output for the user of the ventilator or there is an automatic selection and application of this ventilation setting.

The invention also relates to an apparatus for capturing the electrical behavior of a living body during respiration and/or ventilation, which comprises ventilation elements, elements for capturing the impedance of the living body and at least one control unit. The impedance is captured using at least two electrically conductive electrodes, which capture the electrical behavior of the living body. The elements for capturing the impedance are configured to capture the change in the impedance of the living body over time during respiration and/or ventilation. The ventilation elements are configured to stipulate respiratory gas volumes for inspiration and expiration. The control unit, at least intermittently, evaluates information items about the impedance and information items about the respiration and/or ventilation. A first ventilation setting is stipulated for at least one instance of respiration and/or ventilation and, in the process, a first impedance variation is ascertained and, subsequently, a second ventilation setting is stipulated for at least one instance of respiration and/or ventilation and, in the process, the one second impedance variation is ascertained and at least the first and the second (or any further) impedance variations are compared to one another and a recommendation for the ventilation setting that causes the highest impedance variation is stored or output for the user of the ventilator or there is an automatic selection and application of this ventilation setting.

The above apparatus may also be characterized in that the apparatus has an integral design and comprises ventilation elements, elements for capturing the impedance and the control unit.

The apparatus may also be characterized in that the apparatus has a multi-part design and the ventilation elements and the elements for capturing the impedance and the control unit are disposed in spatially separated fashion and interact in functional fashion.

The invention also relates to an apparatus for capturing the electrical behavior of a living body during respiration and/or ventilation, which comprises ventilation elements, elements for capturing the impedance of the living body and at least one control unit. The impedance is captured using at least two electrically conductive electrodes, which capture the electrical behavior of the living body, the elements for capturing the impedance being configured to capture the change in the impedance of the living body over time during respiration and/or ventilation. The ventilation elements are configured to stipulate respiratory gas volumes for inspiration and expiration. The apparatus is characterized in that the control unit determines the slope of the (current) impedance, the slope being able to adopt positive and negative values (polarity of the slope) or being able to equal zero.

As an alternative and/or in addition thereto, the invention also relates to a method and an apparatus for quickly and effectively ascertaining the electrical impedance (EI) over time during respiration/ventilation, with ascertainment of an image information item of the electrical impedance (distribution).

BRIEF DESCRIPTION OF THE DRAWINGS

In the attached drawings:

FIG. 5 schematically shows a profile of the impedance of the thorax during respiration.

DETAILED DESCRIPTION OF EXEMPLARY EMBODIMENTS OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
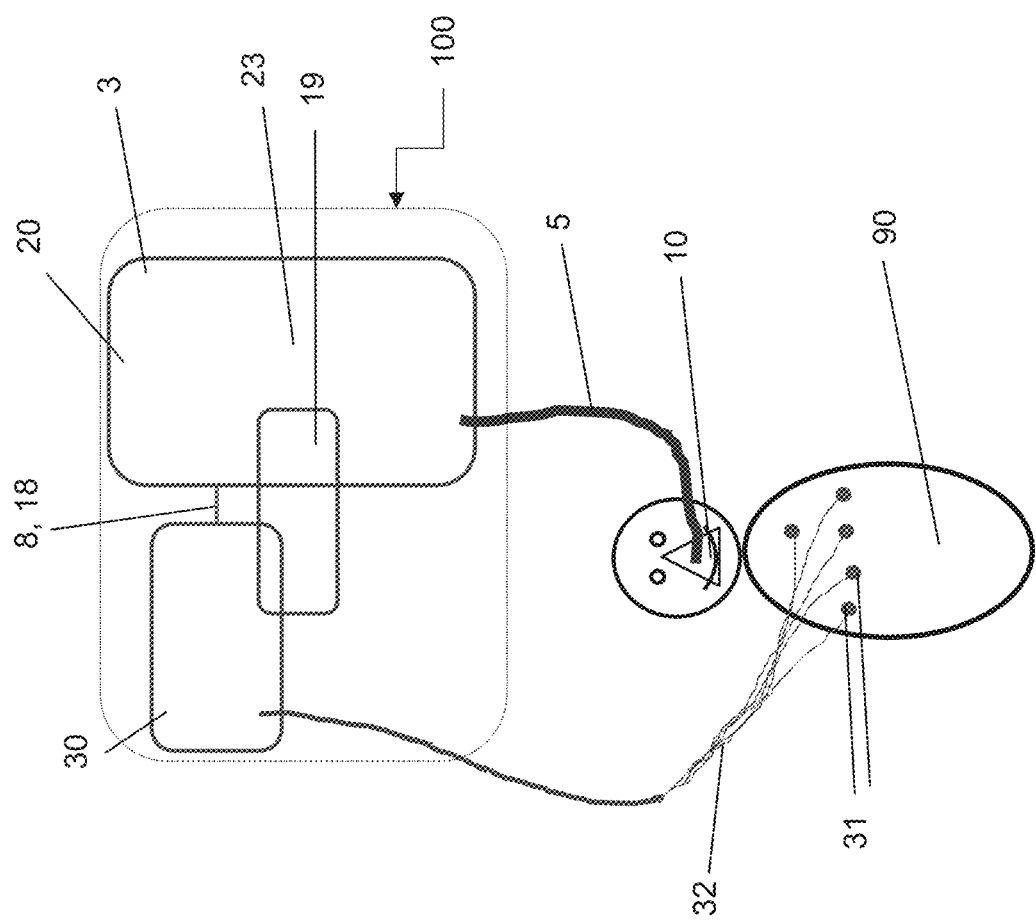
FIG. 1 schematically shows an apparatus according to the invention.

FIG. 1 schematically shows the apparatus (100) with the arrangement of ventilator (20) and impedance monitor (30), which can be part of the ventilator or a separate device that preferably functionally interacts with the ventilator, on the patient (90). The impedance (40) measurement is based on the use of electrically conductive electrodes (31), which actively or passively capture the electrical behavior of the human body (90).

The impedance (40), measured or determined continuously or phase-by-phase, allows the assessment of the change in impedance of the thorax during respiration or under ventilation.

In the case of the impedance monitor (30) according to the invention, an electric current is applied to the skin of the thorax in order to build up an electric field in the thorax. According to the invention, 2, 4, 8, 16, 32 or more electrodes (31) may be arranged around the thorax and used for measuring the electric potentials resulting from the field. The measured voltages are used to ascertain the change in the electrical impedance in the thorax using algorithms. Dispensing with an ascertainment of the impedance distribution and dispensing with a complicated calculation of image data allow a very quick and cost-effective use of the impedance information item.

According to the invention, changes in the impedance may be ascertained relative to a base or reference determination. By way of example, the change in the impedance over the course of respiration/ventilation is ascertained thus, the impedance rising with inspiration and falling with expiration. This relative approach eliminates errors that arise from assumptions in respect of the thorax shape, electrode position and body composition, as are conventional in EIT technology. Consequently, the changes in the impedance do not indicate the absolute value of the latter.

According to the invention, restricted amounts of current (typically 0.5-100 mA) are used since only small currents obtain a maximum signal-to-noise ratio. The electrodes are distributed at discrete physical locations around the thoracic cage or on the thoracic cage, for example with equidistant spacings.

The electrodes (31) can be insulated gel electrodes or ECG electrodes, which are connected to distantly arranged electronic circuits by individual shielded cables.

Figure 2:
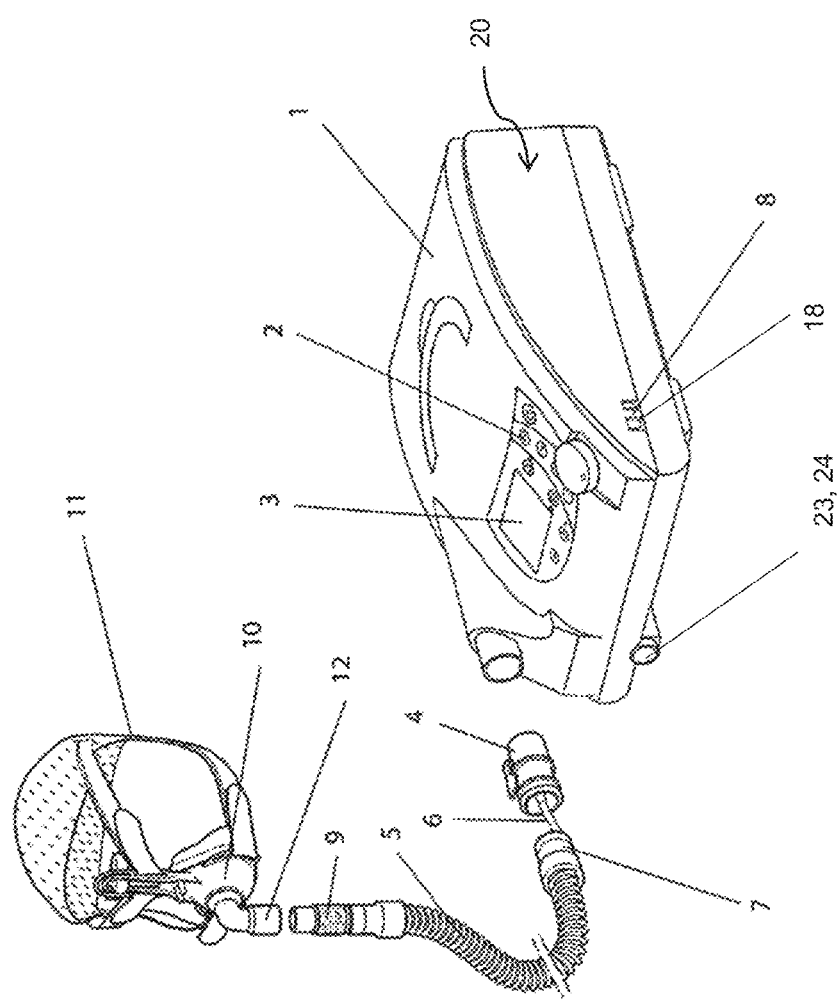
FIG. 2 shows the basic setup of a ventilator and a patient interface embodied as a ventilation mask.

FIG. 2 shows the basic setup of a ventilator (20). An operating element (2) and/or an operation and information system (3) are disposed in the region of a device housing (1). A connecting tube (5) is connected by way of a coupling (4). An additional pressure measuring tube (6) can extend along the connecting tube (5), said additional pressure measuring tube being connectable to the device housing (1) by way of a pressure input nozzle (7). For the purposes of facilitating data transfer, the device housing (1) comprises at least one interface (8, 18). A humidifier (21) or a nebulizer (22) can moreover be adapted. The ventilator comprises a respiratory gas source (17).

An expiratory element (9) is disposed for example in the region of an extent of the connecting tube (5) distant from the device housing (1). An exhalatory valve can likewise be used.

The ventilator (20) can be embodied as a sleep therapy device, as a high-flow device, as an anesthesia device, as a clinical or home ventilator or as a resuscitator.

Moreover, FIG. 2 shows a patient interface embodied as a ventilation mask (10). Attachment in the region of the head of a patient can be implemented by way of a headgear (11). In the region of its extent facing the connecting tube (5), the patient interface (10) comprises a coupling element (12). By way of example, the patient interface can also be embodied as a tube or any other interface.

Data, such as relating to the dead-space volume, for example, can be input and/or output by the interface (8, 18). The interfaces can be realized as wired interfaces, infrared interfaces, Bluetooth interfaces or USB. Preferably, a card slot is also provided. The interface (8) can also be embodied as a LAN interface or as any other interface for connection to the Internet or to a patient monitor or to an EI device (30). An oxygen supply valve can be adapted to the ventilation apparatus in the region of a device housing. Enriching the respiratory gas additionally with oxygen in order to improve the patient care is conceivable.

The ventilator (20) according to the invention is configured in such a way that it can be connected to a patient by way of a tube and a patient interface so as to provide ventilation. It comprises a source for respiratory gas (17), which is embodied as an electric motor with an impeller or as a pressurized gas connector with at least one valve, for example. The ventilator comprises a device for establishing pressure and/or flow and/or volume (23, 24) of the respiratory gas. A control unit (19) is designed in such a way that it determines, e.g., for each respiratory cycle, a respiratory gas pressure on the basis of a predetermined value and/or on the basis of measurement signals for the pressure and/or flow and/or volume parameters, and regulates the source for respiratory gas in such a way that the respiratory gas parameter is applied. The control unit can stipulate the parameters of ventilation in controlled fashion and/or at least partly in assisted or adaptive fashion, taking account of measurement signals.

By way of example, the control unit (19) is configured in such a way that it determines the current pressure and/or flow and/or the volume of respiratory gas. The current value can be presented on the display (3).

Furthermore, the control unit (19) compares those parameter values which have been predetermined by a user, e.g. upper and lower pressure limits or a maximum tolerable number of apneas per unit time, or a maximum tolerable leakage, with the current values and generates a user information item in relation to deviations from the specification. The user information is preferably visualized graphically by way of the operation and information system (3).

To this end, the ventilator (20) comprises a (pneumatic or electronic or optical) pressure measuring input and a pressure sensor (23).

By way of example, the control unit (19) is configured and embodied to identify a change in the impedance and, thereupon, control the ventilator to stipulate a ventilation parameter.

When a threshold for the impedance is overshot or undershot, the control unit (19) generates, for example, a control signal for the ventilator (20) for stipulating an inspiratory or expiratory respiratory gas pressure. When a threshold for the impedance is overshot or undershot, the control unit (19) generates, for example alternatively, a control signal for the ventilator (20) for terminating the stipulation of an inspiratory or expiratory respiratory gas pressure.

Figure 3:
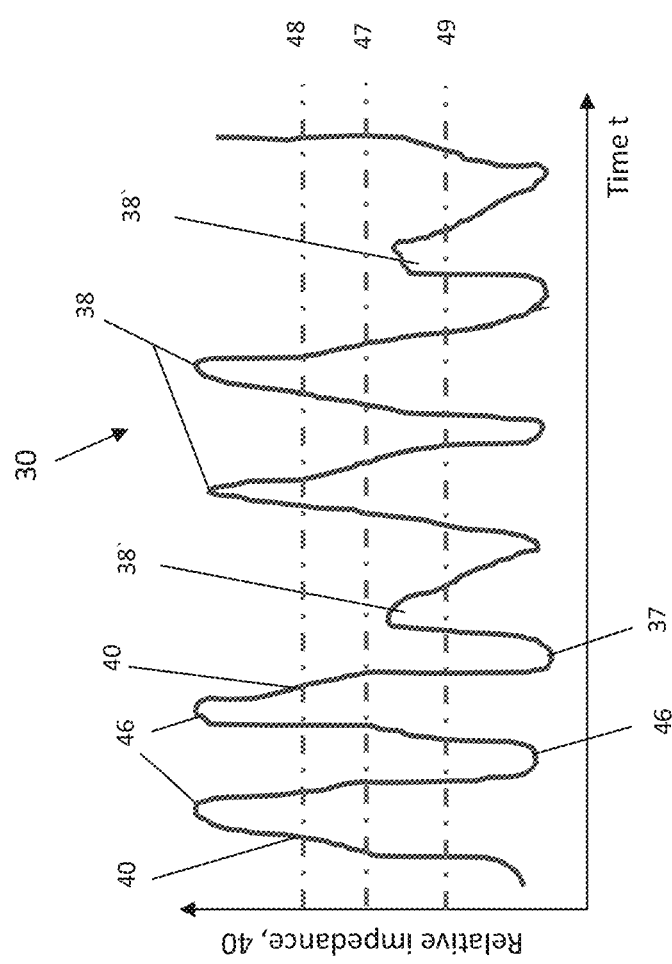
FIG. 3 schematically shows a curve of the impedance of the thorax during respiration.

FIG. 3 schematically shows the curve of the impedance (40) of the thorax during respiration. The curve of the summed signal of the impedance is illustrated, the summed signal increasing with inspiration (38, 38') and falling with expiration. Here, the impedance is plotted without units as a relative impedance (40). The impedance monitor (30) captures the impedance (40), for example of the thorax, at a rate of, e.g., 6-200 measurements per second. From the measured values, the software creates the relative impedances (40).

The impedance alternates between values of maximum (38) and minimum (37) impedance with the rhythm of the respiration/ventilation. Continuously recording the impedance allows a determination of the slope (45) of the (current) impedance at any time. Here, the slope can assume positive and negative values (polarity of the slope). It is evident that the slope (45) reduces and eventually reaches a point at which the slope is substantially zero (46) when approaching a value of maximum (38) or minimum (37) impedance, and that said slope subsequently increases again.

Therefore, the control unit (19) is preferably configured to determine the slope (45) of the impedance (40). The control unit (19) is also configured to determine the polarity of the slope.

Therefore, the control unit (19) is preferably also configured to capture a change in the slope (45) of the impedance (40). The control unit (19) is also configured to capture a flattening of the slope (45) of the impedance (40), the controller interpreting a flattening of the slope (45) as an approach to a value of maximum (38) or minimum (37) impedance. Following identification of a flattening of the slope (45) of the impedance (40), the control unit (19) is also configured to ascertain the transition to a point at which the slope is substantially zero (46) and subsequently increases again. The control unit (19) is also configured to interpret such points at which the slope is substantially zero (46) as end-expiratory impedance (37) and/or as end-inspiratory impedance (38). The control unit (19) is also configured to identify a flattening of the slope (45) of the impedance (40) (which may tend to zero (46)) in the case of a slope with a first polarity and subsequently identify a slope with a second polarity. The control unit (19) is also configured to interpret the change in the polarity of the slope as the region of an end-expiratory impedance (37) or an end-inspiratory impedance (38). The control unit (19) is also configured to interpret the change in the polarity of the slope as the region of a trigger time. The control unit (19) is also configured to determine whether inspiration or expiration is present from the polarity of the slope.

By way of example, the end-expiratory impedance (37) and/or the end-inspiratory impedance (38) is considered for the further evaluation. The end-inspiratory impedance (38) is the impedance at the end of an instance of inspiration. A threshold (48) can be set and/or automatically ascertained for the inspiratory impedance (38). Inspiratory impedances (38) that lie below the threshold (48) are assessed as failed triggers (38'). Here, inspiratory effort by the patient does not lead to inspiration (by the ventilator).

A threshold (49) for minimum expiratory impedance (37) can also be defined and used in analog fashion.

The threshold could also be the mean impedance (47). According to the invention, the failed triggers (38') are registered and stored and/or transmitted to the ventilator (20) and/or impedance monitor (30). The failed triggers (38') can be directly visualized in the region of a display (3) or stored in recallable fashion by the ventilator (20) and/or the impedance monitor (30).

According to the invention, the failed triggers (38') can be stored and output as a number of failed triggers (38') per unit time. According to the invention, the threshold (48, 49) is set in advance and/or can be set by the user and/or said threshold is auto-adaptively adjustable, at least in part, on the basis of at least the maximum impedance. The threshold (48, 49) can lie at a percentage of the maximum impedance (38), for example in the range of 66% to 33% of the maximum impedance (38) or in the range below 75% of the maximum impedance (38) or in the range below 50% of the maximum impedance. The threshold (48, 49) could also be set on the basis of the minimum impedance (37); by way of example, the minimum impedance (37) must be exceeded by at least 40% or exceeded by at least 70% so as not to deduce a failed trigger (38').

According to the invention, it is also considered to use the failed triggers (38') to modify the ventilation settings, such as, e.g., pressure, frequency and volume, and the sensitivity of the sensors in an adaptive fashion so that the number of failed triggers (38') is reduced.

Figure 4:
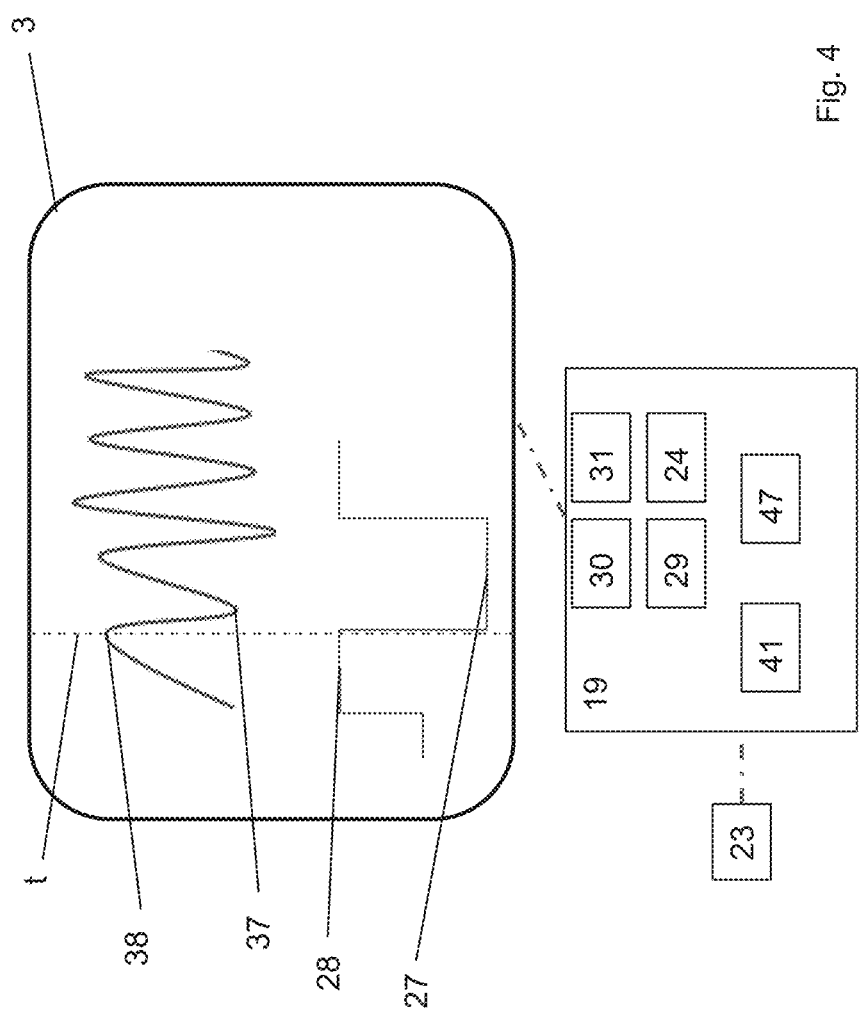
FIG. 4 schematically shows a profile of the impedance of the thorax during respiration in the region of a display at the top.

FIG. 4 schematically shows the profile of the impedance (40) of the thorax during respiration in the region of a display (3) at the top. For the further evaluation, the end-expiratory impedance (37), the end-inspiratory impedance (38) is displayed, for example.

Moreover, the bottom part of the display (3) shows the profile of targets for the ventilator or measured values of the sensors, which correspond to the pressure profile here, with inspiratory pressures (28) and expiratory pressures (27). Plotted likewise is a time information item (t), which visually connects the curves of the impedance and the ventilation target. In particular, the control unit (19) is evident in the lower part of FIG. 4, said control unit collecting and preparing the necessary measured values and information items for presenting the profile of the change in the impedance (40) and the ventilation/respiration.

FIG. 5 schematically shows the profile of the impedance (40) of the thorax during respiration. Here, the impedance is plotted without units as a relative impedance (40). The impedance monitor (30) captures the impedance (40), for example of the thorax, at a rate of, e.g., 60 (or in the range of 20-100) measurements per second. The software creates the relative impedances (40) from the measured values and reproduces said relative impedances as numerical values, for example. For the further evaluation, use is made of, e.g., the end-expiratory impedance (37), the end-inspiratory impedance (38) and the impedance variation (39).

The impedance variation (39) is the difference between end-expiratory (lowest) impedance and end-inspiratory (highest) impedance; it represents the change in the thoracic impedance when taking a breath. An increase in the impedance variation (39) indicates an increase of the respiratory gas volume. In very much simplified terms, the ventilation of the lung is then improved.

The end-expiratory impedance (37) is the impedance at the end of expiration. The end-inspiratory impedance (38) is the impedance at the end of inspiration.

According to the invention, it is also considered to use the end-expiratory impedance (37) to adaptively modify the ventilation settings, such as, e.g., pressure, PEEP, the pressure control during expiration, frequency, volume and/or the sensitivity of the sensors, so that the end-expiratory impedance (37) is reduced.

According to the invention, it is also considered to use the end-expiratory impedance (37) for setting the optimal PEEP. To this end, a first PEEP pressure is stipulated for at least one breath or for a plurality of breaths and a first end-expiratory impedance (37) is ascertained in the process. Then, a second PEEP pressure is stipulated for at least one breath or for a plurality of breaths and a second end-expiratory impedance (37) is ascertained in the process. According to the invention, a multiplicity of PEEP pressures can be stipulated within this meaning and a multiplicity of corresponding end-expiratory impedances (37) can be ascertained. At least the first and the second (or any further) end-expiratory impedances (37) are then compared with one another. A recommendation for the PEEP pressure (41best) causing the smallest end-expiratory impedance (37best) is stored or output for the user of the ventilator or there is an automatic selection and application of this PEEP pressure (41best).

To this end, different PEEP pressures are systematically stipulated for at least one breath or for a plurality of breaths.

According to the invention, it is also considered to use an end-inspiratory impedance (38) to adaptively modify the ventilation settings, such as, e.g., pressure, PEEP, the pressure control during inspiration, frequency, volume and/or sensitivity of the sensors, so that the end-inspiratory impedance (38) increases.

From the change in the end-expiratory impedance (37) and end-inspiratory impedance (38) over time, the impedance monitor is able to determine the frequency (35) of the respiration/ventilation.

The highest end-inspiratory impedance (38) can be used as a trigger criterion (34) for controlling the subsequent expiration by the ventilator (20).

The lowest end-expiratory impedance (37) can be used as a trigger criterion (34) for controlling the subsequent inspiration by the ventilator (20).

The impedance variation (39) reflects the ventilation changes in the lung. According to the invention, there can be a consideration of the entire lung or else separate evaluation of ventral and dorsal, or arbitrary, lung portions. An increase in the impedance variation (39) indicates an increase in the respiratory gas volume.

According to the invention, it is also considered to use the impedance variation (39) to adaptively modify the ventilation settings, such as, e.g., pressure, PEEP, the pressure control during expiration, frequency, volume and/or sensitivity of the sensors, so that the impedance variation (39) increases.

To this end, a first PEEP pressure is stipulated for at least one breath or for a plurality of breaths and a first impedance variation (39) is ascertained in the process. Then, a second PEEP pressure is stipulated for at least one breath or for a plurality of breaths and a second impedance variation (39) is ascertained in the process. According to the invention, a multiplicity of PEEP pressures can be stipulated within this meaning and a multiplicity of corresponding impedance variations (39) can be ascertained. At least the first and the second (or any further) impedance variations (39) are then compared with one another. A recommendation for the PEEP pressure (41c) causing the highest impedance variation (39c) is stored or output for the user of the ventilator or there is an automatic selection and application of this PEEP pressure (41c).

According to the invention, it is also considered to use the impedance variation (39) to adaptively modify at least one ventilation setting (42), such as, e.g., pressure, PEEP, the pressure control during expiration, frequency, volume and/or sensitivity of the sensors, so that the impedance variation (39) increases.

To this end, a first ventilation setting (42) is stipulated for at least one breath or for a plurality of breaths and a first impedance variation (39) is ascertained in the process. Then, a second ventilation setting (42) is stipulated for at least one breath or for a plurality of breaths and a second impedance variation (39) is ascertained in the process. According to the invention, a multiplicity of ventilation settings (42) can be stipulated within this meaning and a multiplicity of corresponding impedance variations (39) can be ascertained. At least the first and the second (or any further) impedance variations (39) are then compared with one another. A recommendation for the ventilation setting (42a) causing the highest impedance variation (39a) is stored or output for the user of the ventilator or there is an automatic selection and application of this ventilation setting (42a).

What is claimed is:

1. An apparatus for capturing the electrical behavior of a living body during respiration and/or ventilation, wherein the apparatus comprises ventilation elements, elements for capturing an impedance of the living body, and at least one control unit, the impedance being captured using at least two electrically conductive electrodes, which are configured for being placed on a patient's skin and capture the electrical behavior of the living body, the elements for capturing the impedance being configured to capture a change in the impedance of the living body over time during respiration and/or ventilation, the ventilation elements being configured to stipulate respiratory gas volumes for inspiration and expiration alternately in time, and the at least one control unit, at least intermittently, evaluating information items about the impedance and information items about the respiration and/or ventilation.

2. The apparatus of claim 1, wherein the control unit displays and/or records a curve of the impedance over a course of time of the respiration and/or ventilation.

3. The apparatus of claim 1, wherein the at least one control unit determines a slope of the (current) impedance, the slope being able to adopt positive and negative values (polarity of the slope) or being able to equal zero.

4. The apparatus of claim 3, wherein the at least one control unit is configured to determine whether inspiration or expiration is present from a polarity of the slope.

5. The apparatus of claim 3, wherein the at least one control unit is configured to capture a flattening of the slope of the impedance, interpreting a flattening of the slope as an approach to a value of a maximum impedance or a minimum impedance.

6. The apparatus of claim 3, wherein the at least one control unit is configured to ascertain a transition to a point where the slope is substantially zero following an identification of a flattening of the slope of the impedance and to interpret said point as a value of a maximum impedance or a minimum impedance.

7. The apparatus of claim 1, wherein the at least one control unit classifies maximum values of the impedance as inspiratory impedance and/or classifies minimum values of the impedance as expiratory impedance.

8. The apparatus of claim 7, wherein a threshold is set and/or automatically ascertained for the inspiratory impedance.

9. The apparatus of claim 8, wherein impedances that lie below or above the threshold are assessed as failed triggers.

10. The apparatus of claim 8, wherein inspiratory impedances that lie below the threshold are assessed as failed triggers.

11. The apparatus of claim 8, wherein impedances that lie above a temporally directly preceding minimum value of the impedance but lie below the threshold are assessed as failed triggers.

12. The apparatus of claim 9, wherein the failed triggers are registered and stored and/or transmitted to a ventilator and/or an impedance monitor.

13. The apparatus of claim 9, wherein the failed triggers are directly visualized in a region of a display or stored in recallable fashion by a ventilator and/or an impedance monitor.

14. The apparatus of claim 1, wherein the at least one control unit determines a frequency of respiration/ventilation from a change of increasing and decreasing impedance and over time and/or wherein the at least one control unit ascertains an impedance variation from at least one maximum value of the impedance and at least one minimum value of the impedance.

15. The apparatus of claim 1, wherein the at least one control unit uses an end-inspiratory impedance as a trigger criterion for controlling a subsequent expiration by a ventilator and/or a subsequent inspiration by the ventilator.

16. The apparatus of claim 1, wherein the at least one control unit compares a frequency of a ventilation target with an inherent frequency of a patient, which is determined from the impedance and/or a flow or a pressure, and/or wherein the at least one control unit compares a time of the ventilation target with a time of an impedance signal.

17. The apparatus of claim 1, wherein an impedance information item is used by the at least one control unit to assess a mechanical pressure and volume load under ventilation and accordingly adapts a target of the ventilation.

18. The apparatus of claim 1, wherein a first PEEP pressure is stipulated for at least one instance of respiration and/or ventilation by the at least one control unit and, in the process, a first end-expiratory impedance is ascertained and a second PEEP pressure is stipulated for at least one instance of respiration and/or ventilation and, in the process, a second end-expiratory impedance is ascertained, and at least the first and the second end-expiratory impedances are compared to one another and a recommendation for a PEEP pressure that causes the lowest end-expiratory impedance is stored or output for an operator of a ventilator or there is an automatic selection and application of this PEEP pressure.

19. The apparatus of claim 1, wherein a first ventilation setting is stipulated for at least one instance of respiration and/or ventilation and, in the process, a first impedance variation is ascertained and, subsequently, a second ventilation setting is stipulated for at least one instance of respiration and/or ventilation and, in the process, a second impedance variation is ascertained and at least the first and the second impedance variations are compared to one another and a recommendation for the ventilation setting that causes the highest impedance variation is stored or output for a user of a ventilator or there is an automatic selection and application of this ventilation setting.

20. An apparatus for capturing the electrical behavior of a living body during respiration and/or ventilation, wherein the apparatus comprises ventilation elements, elements for capturing an impedance of the living body, and at least one control unit, the impedance being captured using at least two electrically conductive electrodes, which capture the electrical behavior of the living body, the elements for capturing the impedance being configured to capture a change in the impedance of the living body over time during respiration and/or ventilation, the ventilation elements being configured to stipulate respiratory gas volumes for inspiration and expiration, the at least one control unit, at least intermittently, evaluating information items about the impedance and information items about the respiration and/or ventilation, a first ventilation setting being stipulated for at least one instance of respiration and/or ventilation and, in the process, a first impedance variation being ascertained and, subsequently, a second ventilation setting being stipulated for at least one instance of respiration and/or ventilation and, in the process, a second impedance variation being ascertained and at least the first and the second impedance variations being compared to one another and a recommendation for a ventilation setting that causes the highest impedance variation being stored or output for a user of a ventilator or there being an automatic selection and application of this ventilation setting.

* * * * *